US006222078B1

(12) United States Patent
Mandal et al.

(10) Patent No.: US 6,222,078 B1
(45) Date of Patent: *Apr. 24, 2001

(54) METHOD OF MAKING α-CHLORO-α,α-DIFLUORO AROMATIC COMPOUNDS

(75) Inventors: Sanjay Mandal, Grand Island; Kevin R. Benson, West Seneca; James Franc, North Tonawanda, all of NY (US)

(73) Assignee: Occidental Chemical Corporation, Dallas, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/209,030

(22) Filed: Dec. 10, 1998

(51) Int. Cl.$^7$ .................................................. C07C 17/087
(52) U.S. Cl. ............................................. 570/127; 570/129
(58) Field of Search ..................................... 570/127, 129

(56) References Cited

U.S. PATENT DOCUMENTS

| 4,129,602 | 12/1978 | Sendlak | 260/651 F |
|---|---|---|---|
| 4,130,594 | 12/1978 | Sendlak | 260/651 F |
| 4,183,873 | 1/1980 | Baxamusa et al. | 260/651 F |
| 5,463,088 | * 10/1995 | Lui et al. | 549/362 |
| 5,902,912 | * 5/1999 | Tung et al. | 570/164 |
| 6,150,499 | * 11/2000 | Dolbier, Jr. et al. | 528/397 |

FOREIGN PATENT DOCUMENTS

| 1518857 | 8/1969 | (DE) . | |
|---|---|---|---|
| 9743231 | 11/1997 | (WO) | C07B/39/00 |
| 9935111 | 7/1999 | (WO) | C07C/17/20 |

OTHER PUBLICATIONS

Angelini et al., A new selective Radiofluorinating agent, J. Chem. Soc. Chem. Comm. (12), pp. 924–5, 1986.*
Chow et al., "The Synthesis of 1,1,2,2,9,9,10,10–Octafluoro [2.2] paracyclophane" *The Journal of Organic Chemistry*, vol. 35, pp. 20–22 (1970).
Hasek et al., "The Chemistry of Sulfur Tetrafluoride . . ." *Fluorination of Organic Carbonyl Compounds. . .* , vol. 82, pp. 543–551 (1960).
Fuqua et al., "Synthesis and Chemistry of Several Fluorinated p–Xylenes . . . " *Tetrahedron*, vol. 20, pp. 1625–1632 (1964).

Boudakin, "A Novel Route to m–Aminobenzotrifluoride," *J. Fluorine Chem.*, 36(3), pp. 283–291 (1987).

* cited by examiner

Primary Examiner—Mukund J. Shah
Assistant Examiner—Deepak R. Rao
(74) *Attorney, Agent, or Firm*—Richard D. Fuerle; Anne E. Brookes

(57) ABSTRACT

Disclosed is a method of making an α-chloro-α,α-difluoro aromatic compound. An α,α,α-trichloro aromatic compound having the general formula

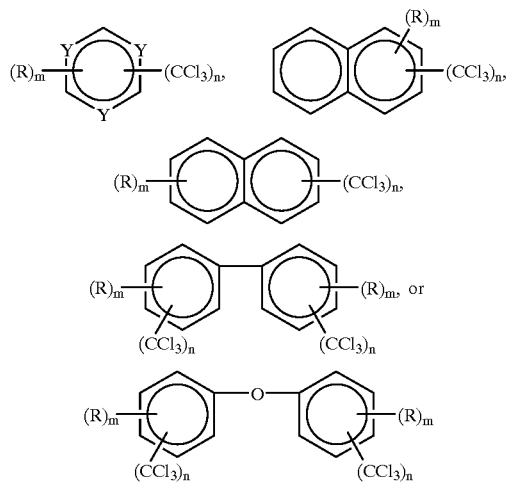

where Y is C or N, R is halogen, R', amino, NHR', NR'$_2$, OR', OCF$_3$, or nitro, R' is alkyl from C$_1$ to C$_{10}$, n is 1, 2, or 3, and m is 0 to 5, is reacted with about 0.7 to about 1.4 equivalents of hydrogen fluoride per chlorine to be replaced, in the presence of about 0.001 to about 1.5 wt %, based on wt % of said α,α,α-trichloro aromatic compound, of a catalyst selected from the group consisting of oxides of Ti, Zr, V, Nb, Ta, Mn, Re, Fe, Ru, Os, Al, Ga, In, Ge, Sn, Sb, and Bi, MoO$_q$X$_r$, (M)$_p$Mo$_{s+t}$O$_{3s+4t}$, (M)$_p$VO$_3$, (M)$_p$VO$_5$, WO$_q$X$_r$, (M)$_p$W$_{s+t}$O$_{3s+4t}$, and mixtures thereof, where M is a cation, X is amine, phosphine, carboxylate, or ketone, p is the negative of the valence of the anion times the inverse of the valence of M, q is 0 to 3, r is 0 to 6, and s is 0 to 4, and t is 1 to 5. Yields of 80% or more were obtained.

20 Claims, No Drawings

METHOD OF MAKING α-CHLORO-α,α-DIFLUORO AROMATIC COMPOUNDS

CROSS-REFERENCE TO RELATED APPLICATION

This application is related to application Ser. No. 09/208,676, filed of even date by S. Mandal et al., titled, "Method of Making α-Chloroxylenes."

BACKGROUND OF THE INVENTION

This invention relates to a method of making an α-chloro-α,α-difluoro aromatic compound, such as α-chloro-α,α-difluoro-toluene, α,α'-dichloro-α,α,α',α'-tetrafluoro-p-xylene (DCTFPX), α,α'-dichloro-α,α,α',α'-tetrafluoro-m-xylene (DCTFMX), α,α',α"-trichloro-α,α,α',α',α,α"-hexafluoro-mesitylene, and α-chloro-α,α-difluoro-naphthalene. In particular, it relates to the reaction of an α,α,α-trichloro aromatic compound with hydrogen fluoride (HF) in the presence of a catalyst to produce the corresponding α-chloro-α,α-difluoro compound.

DCTFPX is a precursor for an inter-layer dielectric material used for making semiconductor chips; it is also a precursor for inert and transparent conformal coatings for electrical components. It has been made by reacting the corresponding dialdehyde with $SF_4$ followed by side-chain chlorination. See "The Synthesis of 1,1,2,2,9,9,10,10-Octafluoro-[2.2]paracyclophane" by S. W. Chow et al., The Journal of Organic Chemistry, vol. 35, pages 20–22 (1970), "The Chemistry of Sulfur Tetrafluoride. II. The Fluorination of Organic Carbonyl Compounds," by W. R. Hasek et al., *J. Amer. Chem. Soc.*; vol. 82, pages 543–551 (1960), and "Synthesis and Chemistry of Several Fluorinated p-Xylenes Designed as Precursors for α,α,α',α'-Tetrafluoro-p-Xylene," by S. A. Fuqua et al., *Tetrahedron*, vol. 20, pages 1625–1632, (1964).

SUMMARY OF THE INVENTION

We have discovered that an α-chloro-α,α-difluoro aromatic compound can be prepared in high yield by reacting the corresponding trichloro compound with hydrogen fluoride in the presence of a particular type of catalyst. For example, DCTFPX and DCTFMX can be prepared by reacting α,α,α,α',α',α'-hexachloro-p-xylene (HCPX) or α,α,α,α',α',α'-hexachloro-m-xylene (HCMX), respectively, with HF in the presence of that catalyst.

We have found that under the conditions of this invention, the predominate reaction is that exactly four of the chlorines on the HCPX or HCMX are replaced with fluorines, two from each of the two pendant groups on the benzene ring, rather than three from one group and one from the other group. The reaction proceeds under relatively mild conditions and is easily controlled.

DESCRIPTION OF THE PREFERRED EMBODIMENTS

The substrates for the process of this invention have the general formula

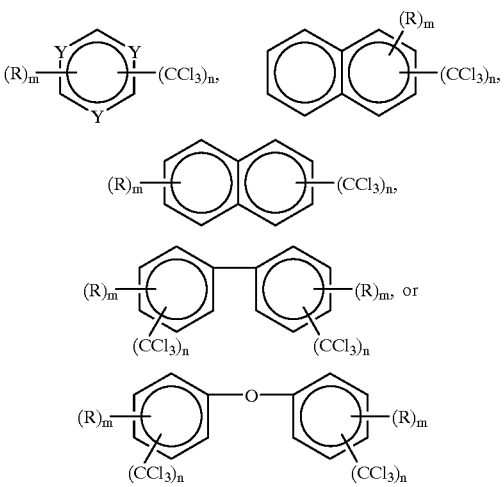

where Y is C or N, each R is independently selected from halogen, R', amino, NHR', NR'$_2$, OR', OCF$_3$, and nitro, R' is alkyl from $C_1$ to $C_{10}$, n is 1, 2, or 3, and m is 0 to 5. Preferably, n is 2 and the R groups are all halogen as the products made from those substrates are commercially more important; m is preferably 0 when n is 2. If n is 2, the two trichloromethyl groups are preferably meta or para. Examples of such substrates include benzotrichloride (BTC), HCPX, HCMX, and α,α,α,α',α',α',α,α,α"-nonachloromesitylene. HCPX and HCMX are the most important substrates. HCPX has the following structure:

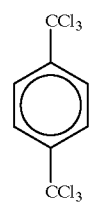

When it is reacted with HF, DCTFPX is produced:

While some tri and penta fluorinated products are present at the end of the reaction, unexpectedly, very little of the following two products are made:

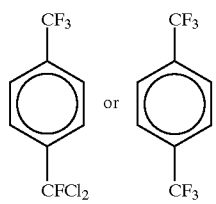

Some of the substrates are commercially available. HCMX and HCPX can be made by reacting m-xylene or p-xylene, respectively, with chlorine free radicals in a solvent. See U.S. patent application Ser. No. 09/208,676, filed of even date, titled, "Method of Making α-Chloroxylenes," herein incorporated by reference, which discloses the chlorination of xylenes. In that patent application, the chlorine free radicals are generated in situ using ultraviolet light or a chlorine free-radical initiator, such as α,α'-azobisisobutynitrile (AIBN) or α,α'-azobis (cyclohexanecarbonitrile) (sold by Dupont as "VAZO-88"). The reaction temperature can be about 70 to about 160° C., but the best results were obtained at about 80 to about 90° C. Heating at reflux is also preferred as that reduces ring chlorination. The preferred solvents are toluene, ring halo subtituted toluene, benzotrifluoride (BTF) and α,α,α,α',α', α'-hexafluoroparaxylene (HFPX) or α,α,α,α',α',α'-hexafluorometaxylene (HFMX), but other solvents can also be used. No base is added to the reaction. At the end of the reaction, a mixture of HCPX or HCMX and the solvent is recovered. The solvent used in the chlorination reaction can be used in the fluorination reaction without separating it, which eliminates processing steps.

The substrate can be melted and reacted with HF gas in the absence of a solvent. The reactor is preferably heated above the melting point of the substrate, e.g., to about 115 to about 120° C. for HCPX. The substrate is placed in the reactor, the catalyst is added, the reactor is closed and heated, and HF gas is admitted to so the reactor. The HF gas can be added even if the substrate is not yet fully melted. As the reaction proceeds, the temperature can be gradually reduced to about 40 to about 85° C., but preferably to about 50 to about 70° C. At lower temperatures more overfluorinated products are formed, reducing the yield of dichlorotetrafluoro product, and at higher temperatures HF efficiency is poor. The reaction can be followed by gas chromatography (GC) to determine when the yield of the dichlorotetrafluoro product is maximized.

It is preferable to use a solvent because a solvent reduces the build up of solids in the reactor condenser. Any organic solvent that is inert in this reaction (including solvents that fluorinate to an inert solvent, such as benzotrichloride, BTC), dissolves the substrate, or forms a slurry with the substrate and boils at a temperature higher than about 70° C. is suitable. Examples of such solvents include BTC, BTF, ring halo substituted BTC and BTF, such as orthochlorobenzotrifluoride (OCBTF), metachlorobenzotrifluoride (MCBTF), parachlorobenzotrifluoride (PCBTF), and 3,4-dichlorobenzotrifluoride (3,4-DCBTF), HFPX, HFMX, toluene, xylenes, mesitylenes, and ring halo substituted toluene, xylenes, mesitylenes, and mixtures thereof; BTF, HFPX, and HFMX are preferred. Low boiling products, such as chloropentafluoroxylenes, dichlorotetrafluoroxylenes, trichlorotrifluoroxylenes, tetrachlorodifluoroxylenes, and mixtures thereof can also be used as solvents. If a solvent is used, the substrate can be added as a powdered solid to the solvent, or added in solution. A solution is preferred as this simplifies operations and the reaction will occur at a lower temperature, which reduces the amount of HF and organics that are condensed. Other advantages to using a solvent include better HF efficiency, increased throughput, less environmental cleanup since very little organic and HF reach the scrubber solution, and problems associated with solids, such as plugging in the condenser and pipes and variations in the temperature of the reactor, are avoided. The percent solids in the solution can be about 10 wt % to about 95 wt %; a lower percent solids is not beneficial due to lower reactor throughput or a slower rate of reaction; preferably, the percent solids is about 30 to about 80. If a solvent is present, the reaction can be started at about 60 to about 105° C., then lowered to about 40 to about 85° C., but preferably to about 50 to about 70° C., after about one equivalent of HF has been added.

About 0.7 to about 1.4 equivalents of HF are used per equivalent of chlorine to be substituted. If less than 0.7 equivalents of HF are used, the product yield falls and more than 1.4 equivalents is unnecessary. It is preferable to use about 0.9 to about 1.25 equivalents of HF per equivalent of chlorine to be substituted. To avoid condensation of the HF, the reactor should be heated prior to its addition.

Catalysts that promote this reaction include oxides of Ti, Zr, V, Nb, Ta, Mn, Re, Fe, Ru, Os, Al, Ga, In, Ge, Sn, Sb, and Bi, $MoO_qX_r$, $(M)_pMo_{s+t}O_{3s+4t}$, $(M)_pVO_3$, $(M)_pVO_5$, $WO_qX_r$, $(M)_pW_{s+t}O_{3s+4t}$, and mixtures thereof, where M is a cation, X is amine, phosphine, carboxylate, or ketone, p is the negative of the valence of the anion times the inverse of the valence of M, q is 0 to 3, r is 0 to 6, s is 0 to 4, and t is 1. to 5. Examples of M include alkali metals, alkaline earth metals, transition metals, lanthanides, gallium, indium, thallium, tin, lead, antimony, bismuth, hydrogen, ammonium, ammonium-hydrogen, alkyl ammonium from $C_1$ to $C_4$, aryl ammonium from $C_6$ to $C_{10}$, phosphonium, alkyl phosphonium from C, to $C_4$, and aryl phosphonium from $C_6$ to $C_{10}$. Preferably, M is alkali metal, alkaline earth metal, hydrogen, ammonium, or ammonium-hydrogen, because these catalysts are commercially available. Examples of the $MoO_qX_r$ catalysts include $MoO_2$, $MoO_3$, and $MoO_2[OC(CH_3):CHCO(CH_3)]_2$. The preferred catalysts are $MoO_2$, $MoO_3$, and $MgMoO_4$, as they were the most selective and the most preferred catalysts are $MoO_3$, $MgMoO_4$, and $MoO_2$. About 0.001 to about 1.5 wt % of catalyst should be used, based on the weight of the substrate; less than 0.01 wt % results in a slow reaction and more than 0.8 wt % may lower the yield due to the formation of over-fluorinated byproducts. The preferred amount of catalyst is about 0.1 to about 0.4 wt %, based on the weight of the substrate, as the maximum yield was observed within that range.

It is preferable to use a condenser on the reactor to condense and return HF, solvents, and organics to the reactor. After the reaction is complete, the contents of the reactor can be passed through basic alumina or soda ash or washed with water to remove HCl, HF, and the catalyst (or the catalyst can be filtered off). The product mixture can be distilled under vacuum to purify and recover the desired product. Because the replacement of each chlorine by a fluorine lowers the boiling point of the product by about 32° C., the trifluorinated, tetrafluorinated, pentafluorinated, and hexafluorinated products can be easily separated by distillation.

The following examples further illustrate this invention.

EXAMPLE 1

Into a 500 mL polytetrafluoroethylene reactor equipped with a magnetic stirring bar, condenser, thermocouple, sample port, and an inlet for HF was placed 250 g (0.8 mol) of pure HCPX, 250 g BTF, and 1.0 g (0.0054 mol or 0.4 wt % based on HCPX) $MgMoO_4$. The reactor was heated to about 95° C. while maintaining the condenser temperature at −25° C. using a chiller. The reaction mixture turned blue. With constant stirring, HF gas was introduced into the reactor at an initial rate of 50 cc/min, which was slowly increased to 200 cc/min for the rest of the reaction. After introducing about one equivalent of HF to the reactor, the reaction temperature was gradually decreased to about 70° C. and maintained at that temperature for the rest of the reaction. A total of 79 g (3.95 mol) of HF was added to the reactor. The reaction was monitored by GC to stop it at the maximum concentration of DCTFPX in the mixture. When the reaction was complete, both HF gas flow and heating were turned off. Nitrogen gas was purged through the reactor until all of the HF had been removed, then the reactor was opened to purify and isolate the product. An assay of the reaction mixture (excluding solvent peak) by GC showed 87 wt % DCTFPX.

The crude mixture was run through a column packed with either basic alumina or sodium carbonate or was washed with distilled water followed by distillation to obtain about 98% pure DCTFPX.

EXAMPLE 2

Example 1 was repeated except that the reactor was charged with 253 g —(0.81 mol) of pure HCPX, 251 9 BTF, and 0.63 g (0.0044 mol or 0.25 wt % based on HCPX) $MoO_3$. A total of 66.7 9 (3.34 mol) of HF was added to the reactor. A GC analysis of the final mixture (excluding solvent peak) showed 82 wt % DCTFPX.

EXAMPLE 3

Example 1 was repeated except that the reactor was charged with 217 9 (0.69 mol) of pure HCPX, 217 g BTF, and 0.89 g (0.0062 mol or 0.4 wt % based on HCPX) $MoO_3$. The reaction temperature was gradually decreased from 95 to 50° C., instead of to 70° C., and a total of 55.3 g (2.76 mol) of HF (at a rate of 300 cc/min) was added to the reactor. An assay of the reaction mixture (excluding solvent peak) by GC showed 77 wt % DCTFPX.

EXAMPLE 4

Example 1 was repeated using a 65:35 molar mixture of HCPX:BTF (313 g HCPX and 169 9 BTF), 0.47 g $MoO_3$ (0.0032 mol. 0.15 wt %), and 80 g of HF (4 mol). An assay of the reaction mixture (excluding solvent peak) by GC showed 86.5 wt % DCTFPX.

EXAMPLE 5

Example 1 was repeated except that the reactor was charged with a 80:20 weight mixture of HCPX:BTF (375 9 (1.2 mol) HCPX and 95 9 BTF), and 0.37 g (0.0026 mol or 0.1 wt % based on HCPX) $MoO_3$. A total of 80.6 g (4.03 mol) of HF (at a rate of 150 cc/min) was added to the reactor. The reaction produced 80 wt % DCTFPX (excluding solvent peak).

EXAMPLE 6

Comparative

Example 1 was repeated except that the reactor was charged with 250 g (0.8 mol) of pure HCPX, 250 g BTF, and 0.5 g (0.0025 mol or 0.2 wt % based on HCPX) $MoO_2Cl_2$. A total of 84 g (4.2 mol) of HF was added to the reactor. A GC analysis of the final mixture (excluding solvent peak) showed 77 wt % DCTFPX.

EXAMPLE 7

Comparative

Example 1 was repeated except that the reactor was charged with 232 g (0.74 mol) of pure HCPX, 232 g BTF, and 0.215 g (0.00079 mol or 0.09 wt % based on HCPX) $MoCl_5$. A total of 78.9 g (3.94 mol) of HF was added to the reactor. A GC analysis of the final mixture (excluding solvent peak) showed 72 wt % DCTFPX.

EXAMPLE 8

Example 1 was repeated except that the reactor was charged with 210 g (0.67 mol) of pure HCPX, 210 g PCBTF, and 0.777 g (0.0054 mol or 0.37 wt % based on HCPX) $MoO_3$. A total of 77 g (3.85 mol) of HF was added to the reactor; GC analysis of the final mixture (excluding solvent peak) showed 82 wt % DCTFPX.

EXAMPLE 9

Example 1 was repeated except that the reactor was charged with 312.7 g (1 mol) of pure HCPX, 313.1 9 BTF, and 2.196 g (0.0172 mol or 0.7 wt % based on HCPX) $MoO_2$. A total of 128 g (6.4 mol) of HF was added at a rate of 150 cc/min to the reactor; GC analysis of the final mixture (excluding solvent peak) showed 81 wt % DCTFPX.

EXAMPLE 10

Into a 500 mL polytetrafluoroethylene reactor equipped with a magnetic stirring bar, a condenser, a thermocouple, a sample port, and an inlet for HF was placed 413 g (1.32 mol) of HCPX and 1.61 g (0.011 mol or 0.39 wt % based on HCPX) of $MoO_3$. The reactor was heated to 115–120° C. using an oil bath, while the condenser temperature was maintained at 85 to 90° C. using a water bath. The tubing between the reactor and the condenser was also heated to 90 to 105° C. using a heating tape. With constant stirring, HF gas was introduced to the reactor at an initial rate of 50 cc/min, which was slowly increased to 300 cc/min for the rest of the reaction. As the hydrofluorination continued, the reaction temperature was gradually decreased to about 60° C. with a gradual decrease of the condenser temperature to 10° C. A total of 240 g (12 mol) of HF was added to the reactor. The reaction was stopped after 12 hours and a GC analysis of the final mixture indicated 83 wt % DCTFPX.

The overall HF efficiency was 39.4%. This low HF efficiency could be due to the initial condenser temperature being much higher than the boiling point of HF and thus a portion of HF would be carried with off gas HCl to the scrubber.

We claim:

1. A method of making an α-chloro-α,α-difluoro aromatic compound comprising reacting an α,α,α-trichloro aromatic compound having the general formula

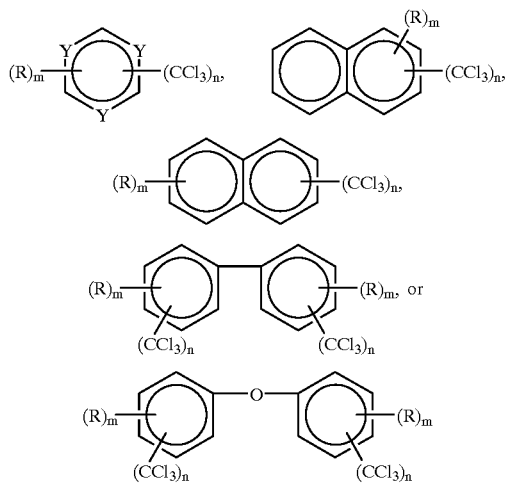

where Y is C or N, R is halogen, R', amino, NHR', NR'$_2$, OR', OCF$_3$, or nitro, R' is alkyl from C$_1$ to C$_{10}$, n is 1, 2, or 3, and m is 0 to 5, with about 0.7 to about 1.4 equivalents of hydrogen fluoride gas per chlorine to be replaced, in the presence of about 0.001 to about 1.5 wt %, based on wt % of said α,α,α-trichloro aromatic compound, of a catalyst selected from the group consisting of oxides of Ti, Zr, V, Nb, Ta, Mn, Re, Fe, Ru, Os, Al, Ga, In, Ge, Sn, Sb, and Bi, $MoO_qX_r$, $(M)_pMo_{s+t}O_{3s+4t}$, $(M)_pVO_3$, $(M)_pVO_5$, $WO_qX_r$, $(M)_pW_{s+t}O_{3s+4t}$, and mixtures thereof, where M is a cation, X is amine, phosphine, carboxylate, or ketone, p is the negative of the valence of the anion times the inverse of the valence of M, q is 0 to 3, r is 0 to 6, s is 0 to 4, and t is 1 to 5, where said α,α,α-trichloro aromatic compound is melted when no solvent is present or said reaction is at about 40 to about 105° C. when a solvent is present.

2. A method according to claim 1 wherein said catalyst is $MoO_3$.

3. A method according to claim 1 wherein said catalysts $MgMoO_4$.

4. A method according to claim 1 wherein said catalyst is $MoO_2$.

5. A method according to claim 1 wherein said α,α,α-trichloro aromatic compound is α,α,α, α',α',α'-hexachloroparaxylene and said α-chloro-α,α-difluoro aromatic compound is α,α'-dichloro-α,α,α',α'-tetrafluoroparaxylene.

6. A method according to claim 1 wherein said α,α,α-trichloro aromatic compound is α,α,α,α',α',α'-hexachlorometaxylene and said α-chloro-α,α-difluoro aromatic compound is α,α'-dichloro-α,α,α',α'-tetrafluorometaxylene.

7. A method according to claim 1 wherein said α,α,α-trichloro aromatic compound is in a solution of an inert organic solvent.

8. A method according to claim 7 wherein said inert organic solvent is selected from the group consisting of hexafluoroparaxylene, hexafluorometaxylene, benzotrifluoride, toluene, xylenes, mesitylenes, ring halo substituted benzotrifluoride, toluene, xylenes, and mesitylenes, and mixtures thereof.

9. A method according to claim 8 wherein said α,α,α-trichloro aromatic compound is α,α,α,α',α',α'-hexachloroparaxylene, including the initial step of preparing said α,α,α,α',α',α'-hexachloroparaxylene by chlorinating paraxylene.

10. A method according to claim 9 wherein said inert organic solvent is toluene or ring halogenated toluene, said solvent is refluxed, and no base is present during chlorination.

11. A method according to claim 7 wherein the percent solids in said solution is about 10 wt % to about 95 wt %.

12. A method according to claim 7 wherein said reaction is begun at about 60 to about 1 05° C. and the temperature is reduced to about 40 to about 85° C. after about one equivalent of hydrogen fluoride gas has been added.

13. A method according to claim 1 wherein said α,α,α-trichloro aromatic compound is melted and reacted with said hydrogen fluoride gas in the absence of solvent.

14. A method according to claim 1 wherein the amount of said hydrogen fluoride gas is about 0.9 to about 1.25 equivalents per chlorine to be replaced.

15. A method according to claim 1 wherein the amount of said catalyst is about 0.1 to about 0.4 wt %, based on wt % of said α,α,α-trichloro aromatic compound.

16. A method of making α,α'-dichloro-α,α,α,α',α'-tetrafluoroparaxylene or α,α'-dichloro-α,α,α,α',α'-tetrafluorometaxylene comprising (A) preparing a solution of about 30 to about 80 wt % of a hexachloroxylene selected from α,α,α,α',α',α'-hexachloroparaxylene and α,α,α,α',α',α'-hexachlorometaxylene, respectively, in an inert organic solvent;

(B) adding to a reactor heated between 50 and 105° C. said solution and about 0.1 to about 0.4 wt %, based on wt % of said hexachloroxylene, of a catalyst selected from the group consisting of oxides of Ti, Zr, V, Nb, Ta, Mn, Re, Fe, Ru, Os, Al, Ga, In, Ge, Sn, Sb, and Bi, $MoO_q$, $(M)_pMo_{s+t}O_{3s+4t}$, $(M)_pVO_3$, $(M)_pVO_5$, $WO_r$, $(M)_pW_{s+t}O_{3s+4t}$, and mixtures thereof, where M is alkali metal, alkaline earth metal, hydrogen, ammonium, or ammonium-hydrogen, p is the negative of the valence of the anion times the inverse of the valence of M, q is 1.5 to 3, r is 2or 3, and s is 0 to 4, and t is 1 to 5; and (C) admitting to said heated reactor about 3.5 to about 5 equivalents of hydrogen fluoride gas.

17. A method according to claim 16 wherein said catalyst is $MoO_3$, $MgMoO_4$, or $MoO_2$.

18. A method according to claim 16 including the step of preparing said hexachloroxylene in said solvent by chlorinating paraxylene or metaxylene, respectively, at reflux in the absence of a base.

19. A method of making α,α'-dichloro-α,α,α',α'-tetrafluoroparaxylene comprising (A) forming a slurry of about 30 to about 80 wt % solids of α,α,α,α',α',α'-hexachloroparaxylene in benzotrifluoride or α,α,α,α',α',α'-hexafluoroparaxylene;

(B) to a reactor fitted with a condenser, adding said slurry and about 0.1 to about 0.4 wt %, based on wt % of said α,α,α,α',α',α'-hexachloroparaxylene, of a catalyst of $MoO_3$, $MgMoO_4$, or $MoO_2$;

(C) heating said reactor to about 60 to about 105° C.;

(D) adding about one equivalent of hydrogen fluoride gas to said reactor;

(E) lowering the temperature of said reactor to about 50 to about 70° C.;

(F) adding an additional about 2.5 to about 4 equivalents of hydrogen fluoride gas to said reactor;

(G) after the reaction is complete, removing the catalyst; and (H) distilling the product mixture from said reactor to recover said α,α'-dichloro-α,α,α',α'-tetrafluoroparaxylene.

20. A method according to claim 19 including the step of preparing said hexachloroxylene in said solvent by chlorinating paraxylene at reflux in the absence of a base.

* * * * *